US009695063B2

(12) United States Patent
Rietman et al.

(10) Patent No.: US 9,695,063 B2
(45) **Date of Patent: *Jul. 4, 2017**

(54) COMBINED ACOUSTIC MICRO FILTRATION AND PHONONIC CRYSTAL MEMBRANE PARTICLE SEPARATION

(71) Applicant: FloDesign Sonics, Inc., Wilbraham, MA (US)

(72) Inventors: Edward A. Rietman, Nashua, NH (US); Bart Lipkens, Hampden, MA (US); Jason Dionne, Simsbury, CT (US)

(73) Assignee: FLODESIGN SONICS, INC, Wilbraham, MA (US)

( * ) Notice: Subject to any disclaimer, the term of this patent is extended or adjusted under 35 U.S.C. 154(b) by 671 days.

This patent is subject to a terminal disclaimer.

(21) Appl. No.: 14/180,663

(22) Filed: Feb. 14, 2014

(65) Prior Publication Data

US 2014/0190889 A1 Jul. 10, 2014

Related U.S. Application Data

(62) Division of application No. 13/216,070, filed on Aug. 23, 2011, now Pat. No. 8,679,338.

(Continued)

(51) Int. Cl.
*C02F 103/08* (2006.01)
*C02F 1/44* (2006.01)

(Continued)

(52) U.S. Cl.
CPC .............. *C02F 1/36* (2013.01); *B01D 21/283* (2013.01); *B01D 61/00* (2013.01); *B01D 61/20* (2013.01); *B01D 65/00* (2013.01); *B01D 65/08* (2013.01); *C02F 1/444* (2013.01); *B01D 2321/2075* (2013.01); *C02F 2103/08* (2013.01); *C02F 2303/04* (2013.01); *C12M 47/02* (2013.01)

(58) Field of Classification Search
None
See application file for complete search history.

(56) References Cited

U.S. PATENT DOCUMENTS

| | | | |
|---|---|---|---|
| 2,667,944 | A | 2/1954 | Crites |
| 3,555,311 | A | 1/1971 | Weber |

(Continued)

FOREIGN PATENT DOCUMENTS

| | | | |
|---|---|---|---|
| DE | 30 27 433 | A1 | 2/1982 |
| EP | 0 292 470 | B1 | 11/1988 |

(Continued)

OTHER PUBLICATIONS

Alvarez et al.; Shock Waves, vol. 17, No. 6, pp. 441-447, 2008.

(Continued)

*Primary Examiner* — Krishnan S Menon
*Assistant Examiner* — Bradley R Spies
(74) *Attorney, Agent, or Firm* — Richard M. Klein; Fay Sharpe LLP

(57) ABSTRACT

A system is provided that includes one or more acoustic microfilters through which is flowed a mixture of a fluid and a particulate to selectively filter particles from the fluid. Also included are one or more phononic crystal units coupled to the acoustic microfilter(s) to further selectively filter particles from the fluid. Related apparatus, systems, techniques and articles are also described.

15 Claims, 8 Drawing Sheets

Related U.S. Application Data

(60) Provisional application No. 61/402,082, filed on Aug. 23, 2010.

(51) Int. Cl.

| | |
|---|---|
| ***B01D 61/00*** | (2006.01) |
| ***B01D 65/08*** | (2006.01) |
| ***C02F 1/36*** | (2006.01) |
| ***B01D 61/20*** | (2006.01) |
| ***B01D 65/00*** | (2006.01) |
| ***B01D 21/28*** | (2006.01) |
| *C12M 1/00* | (2006.01) |

(56) References Cited

U.S. PATENT DOCUMENTS

| | | | |
|---|---|---|---|
| 4,055,491 | A | 10/1977 | Porath-Furedi |
| 4,158,629 | A | 6/1979 | Sawyer |
| 4,165,273 | A | 8/1979 | Azarov et al. |
| 4,173,725 | A | 11/1979 | Asai et al. |
| 4,204,096 | A | 5/1980 | Barcus et al. |
| 4,398,325 | A | 8/1983 | Piaget et al. |
| 4,666,595 | A | 5/1987 | Graham |
| 4,699,588 | A | 10/1987 | Zinn et al. |
| 4,743,361 | A | 5/1988 | Schram |
| 4,759,775 | A | 7/1988 | Peterson et al. |
| 4,983,189 | A | 1/1991 | Peterson et al. |
| 5,085,783 | A | 2/1992 | Feke et al. |
| 5,225,089 | A | 7/1993 | Benes et al. |
| 5,371,429 | A | 12/1994 | Manna |
| 5,395,592 | A | 3/1995 | Bolleman et al. |
| 5,431,817 | A | 7/1995 | Braatz et al. |
| 5,443,985 | A | 8/1995 | Lu et al. |
| 5,452,267 | A | 9/1995 | Spevak |
| 5,484,537 | A | 1/1996 | Whitworth |
| 5,527,460 | A | 6/1996 | Trampler et al. |
| 5,560,362 | A | 10/1996 | Sliwa, Jr. et al. |
| 5,594,165 | A | 1/1997 | Madanshetty |
| 5,604,301 | A | 2/1997 | Mountford et al. |
| 5,626,767 | A | 5/1997 | Trampler et al. |
| 5,688,405 | A | 11/1997 | Dickinson et al. |
| 5,711,888 | A | 1/1998 | Trampler et al. |
| 5,831,166 | A | 11/1998 | Kozuka et al. |
| 5,902,489 | A | 5/1999 | Yasuda et al. |
| 5,912,182 | A | 6/1999 | Coakley et al. |
| 5,951,456 | A | 9/1999 | Scott |
| 6,090,295 | A | 7/2000 | Raghavarao et al. |
| 6,166,231 | A | 12/2000 | Hoeksema |
| 6,205,848 | B1 | 3/2001 | Faber et al. |
| 6,216,538 | B1 | 4/2001 | Yasuda et al. |
| 6,332,541 | B1 | 12/2001 | Coakley et al. |
| 6,391,653 | B1 | 5/2002 | Letcher et al. |
| 6,487,095 | B1 | 11/2002 | Malik et al. |
| 6,592,821 | B1 | 7/2003 | Wada et al. |
| 6,649,069 | B2 | 11/2003 | DeAngelis |
| 6,763,722 | B2 | 7/2004 | Fjield et al. |
| 6,881,314 | B1 | 4/2005 | Wang et al. |
| 6,929,750 | B2 | 8/2005 | Laurell et al. |
| 6,936,151 | B1 | 8/2005 | Lock et al. |
| 7,010,979 | B2 | 3/2006 | Scott |
| 7,061,163 | B2 | 6/2006 | Nagahara et al. |
| 7,081,192 | B1 | 7/2006 | Wang et al. |
| 7,093,482 | B2 | 8/2006 | Berndt |
| 7,108,137 | B2 | 9/2006 | Lal et al. |
| 7,150,779 | B2 | 12/2006 | Meegan, Jr. |
| 7,186,502 | B2 | 3/2007 | Vesey |
| 7,191,787 | B1 | 3/2007 | Redeker et al. |
| 7,331,233 | B2 | 2/2008 | Scott |
| 7,340,957 | B2 | 3/2008 | Kaduchak et al. |
| 7,373,805 | B2 | 5/2008 | Hawkes et al. |
| 7,541,166 | B2 | 6/2009 | Belgrader et al. |
| 7,601,267 | B2 | 10/2009 | Haake et al. |
| 7,673,516 | B2 | 3/2010 | Janssen et al. |
| 7,837,040 | B2 | 11/2010 | Ward et al. |
| 7,846,382 | B2 | 12/2010 | Strand et al. |
| 7,968,049 | B2 | 6/2011 | Takahashi et al. |
| 8,080,202 | B2 | 12/2011 | Takahashi et al. |
| 8,256,076 | B1 | 9/2012 | Feller |
| 8,266,950 | B2 | 9/2012 | Kaduchak et al. |
| 8,273,253 | B2 | 9/2012 | Curran |
| 8,273,302 | B2 | 9/2012 | Takahashi et al. |
| 8,309,408 | B2 | 11/2012 | Ward et al. |
| 8,319,398 | B2 | 11/2012 | Vivek et al. |
| 8,334,133 | B2 | 12/2012 | Fedorov et al. |
| 8,387,803 | B2 | 3/2013 | Thorslund et al. |
| 8,592,204 | B2 | 11/2013 | Lipkens et al. |
| 8,679,338 | B2 | 3/2014 | Rietman et al. |
| 2002/0134734 | A1 | 9/2002 | Campbell et al. |
| 2003/0195496 | A1 | 10/2003 | Maguire |
| 2003/0209500 | A1 | 11/2003 | Kock et al. |
| 2003/0230535 | A1 | 12/2003 | Affeld et al. |
| 2004/0016699 | A1 | 1/2004 | Bayevsky |
| 2005/0196725 | A1 | 9/2005 | Fu |
| 2006/0037915 | A1 | 2/2006 | Strand et al. |
| 2007/0224676 | A1 | 9/2007 | Haq |
| 2007/0272618 | A1 | 11/2007 | Gou et al. |
| 2007/0284299 | A1 | 12/2007 | Xu et al. |
| 2008/0217259 | A1 | 9/2008 | Siversson |
| 2008/0245745 | A1 | 10/2008 | Ward et al. |
| 2009/0029870 | A1 | 1/2009 | Ward et al. |
| 2009/0045107 | A1 | 2/2009 | Ward et al. |
| 2009/0053686 | A1 | 2/2009 | Ward et al. |
| 2009/0098027 | A1 | 4/2009 | Tabata et al. |
| 2009/0178716 | A1 | 7/2009 | Kaduchak et al. |
| 2009/0194420 | A1 | 8/2009 | Mariella, Jr. et al. |
| 2009/0226994 | A1 | 9/2009 | Lemor et al. |
| 2009/0295505 | A1 | 12/2009 | Mohammadi et al. |
| 2010/0000945 | A1 | 1/2010 | Gavalas |
| 2010/0078384 | A1 | 4/2010 | Yang |
| 2010/0124142 | A1 | 5/2010 | Laugharn et al. |
| 2010/0192693 | A1 | 8/2010 | Mudge et al. |
| 2010/0193407 | A1 | 8/2010 | Steinberg et al. |
| 2010/0206818 | A1 | 8/2010 | Leong et al. |
| 2010/0255573 | A1 | 10/2010 | Bond et al. |
| 2010/0261918 | A1 | 10/2010 | Chianelli et al. |
| 2010/0317088 | A1 | 12/2010 | Radaelli et al. |
| 2010/0323342 | A1 | 12/2010 | Gonzalez Gomez et al. |
| 2010/0330633 | A1 | 12/2010 | Walther et al. |
| 2011/0003350 | A1 | 1/2011 | Schafran et al. |
| 2011/0024335 | A1 | 2/2011 | Ward et al. |
| 2011/0092726 | A1 | 4/2011 | Clarke |
| 2011/0095225 | A1 | 4/2011 | Eckelberry et al. |
| 2011/0123392 | A1 | 5/2011 | Dionne et al. |
| 2011/0154890 | A1 | 6/2011 | Holm et al. |
| 2011/0166551 | A1 | 7/2011 | Schafer |
| 2011/0262990 | A1 | 10/2011 | Wang et al. |
| 2011/0281319 | A1 | 11/2011 | Swayze et al. |
| 2011/0309020 | A1 | 12/2011 | Rietman et al. |
| 2012/0088295 | A1 | 4/2012 | Yasuda et al. |
| 2012/0175012 | A1 | 7/2012 | Goodwin et al. |
| 2012/0325727 | A1 | 12/2012 | Dionne et al. |
| 2012/0328477 | A1 | 12/2012 | Dionne et al. |
| 2012/0329122 | A1 | 12/2012 | Lipkens et al. |
| 2013/0175226 | A1 | 7/2013 | Coussios et al. |
| 2013/0277316 | A1 | 10/2013 | Dutra et al. |
| 2013/0284271 | A1 | 10/2013 | Lipkens et al. |
| 2014/0011240 | A1 | 1/2014 | Lipkens et al. |
| 2014/0017758 | A1 | 1/2014 | Kniep et al. |

FOREIGN PATENT DOCUMENTS

| | | | |
|---|---|---|---|
| EP | 1 254 669 | B1 | 11/2002 |
| GB | 2 420 510 | A | 5/2006 |
| WO | WO 87/07178 | A1 | 12/1987 |
| WO | WO 00/41794 | | 7/2000 |
| WO | WO 02/072234 | A1 | 9/2002 |
| WO | WO 2009/111276 | A1 | 9/2009 |
| WO | WO 2009/144709 | A1 | 12/2009 |
| WO | WO 2010/024753 | A1 | 4/2010 |
| WO | WO 2011/023949 | A2 | 3/2011 |
| WO | WO 2011/025890 | A1 | 3/2011 |
| WO | WO 2011/027146 | A2 | 3/2011 |

(56) References Cited

FOREIGN PATENT DOCUMENTS

| | | | |
|---|---|---|---|
| WO | WO 2011/161463 | A2 | 12/2011 |
| WO | WO 2013/043297 | A1 | 3/2013 |
| WO | WO 2013/055517 | A1 | 4/2013 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Seymour et al, J. Chem. Edu., 1990, 67(9), p. 763, published Sep. 1990.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10- 137E/index.html>.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
European Search Report of European Application No. 11769474.5 Dated Oct. 10, 2012.
International Search Report and Written Opinion of International Application No. PCT/US2013/037404 Dated Jun. 21, 2013.
Annex to Form PCT/ISA/206—Communication Relating to the Results of the Partial International Search Report, dated Jul. 18, 2013.
International Search Report and Written Opinion of International Application No. PCT/US2013/050729 Dated Sep. 25, 2013.
International Search Report for corresponding PCT Application Serial No. PCT/US2014/015382 dated May 6, 2014.
International Search Report for PCT Application No. PCT/US2015/024365 dated Sep. 23, 2015.

300

COMBINED ACOUSTIC MICRO FILTRATION AND PHONONIC CRYSTAL MEMBRANE PARTICLE SEPARATION

CROSS-REFERENCE TO RELATED APPLICATIONS

This application is a divisional of U.S. patent application Ser. No. 13/216,070, filed Aug. 23, 2011, now U.S. Pat. No. 8,679,338, which claims priority to U.S. Patent Application Ser. No. 61/402,082, filed on Aug. 23, 2010, the contents of which are hereby fully incorporated by reference.

TECHNICAL FIELD

The subject matter described herein relates to techniques for particle separation using a combination of acoustic micro filtration and phononic crystal membranes.

BACKGROUND

Very small particles, such as micron-sized bacterial spores and oil droplets, can be difficult to separate from host fluids. Porous filters are sometimes used to separate such particles; however, such filters suffer from many defects. For example, the filters can be overly selective by filtering a large array of particles. Conversely, the filters can be too fine which results in selected particles passing through the filters. In either event, such filters require periodic cleaning and/or replacing which can be costly and disruptive to processes using the filters.

SUMMARY

In one aspect, a system is provided that includes at least one acoustic microfilter through which is flowed a mixture of a fluid and a particulate to selectively filter particles from the fluid, and at least one phononic crystal unit coupled to the at least one acoustic microfilter to further selectively filter particles from the fluid.

The acoustic microfilter(s) can include a first flow chamber with an inlet and an outlet through which is flowed the mixture of a fluid and a particulate, two or more ultrasonic transducers embedded in a wall of the first flow chamber or located outside the flow chamber wall, and two or more reflectors corresponding to each transducer located on the opposite wall of the first flow chamber from each corresponding transducer, the combination of each ultrasonic transducer and corresponding reflector forming a standing acoustic wave at a different ultrasonic frequency optimized for a specific range of particle sizes to selectively filter particles in the fluid.

The phononic crystal unit(s) can include an array of parallel spaced tubes, each tube being surrounded by a porous membrane, a second flow chamber with an inlet and an outlet through which is flowed the filter mixture of fluid and particulate after being filtered by the at least one acoustic microfilter, one or more ultrasonic transducers embedded in a wall of the second flow chamber or located outside a second flow chamber wall, and one or more reflectors corresponding to each transducer located on the opposite wall of the second flow chamber from each corresponding transducer, wherein the ultrasonic transducer/reflector pairs in combination with the array of tubes further selectively filter particles from the fluid. The array of tubes can be positioned in the second flow chamber so that the hollow portions of the tubes are in the direction of flow such that the spaces between each of the tubes in the second flow chamber form an interstitial region. The membrane can comprise a desalination polymer. The tubes can be made up of a porous material. The array of tubes can be positioned in a hexagonal array or a linear array.

In some implementations, there are at least two transducers in each phononic crystal unit that cover an entire boundary or side of the second flow chamber. The acoustic microfilter(s) can comprise a two dimensional or a linear array of transducers. In cases in which there are multiple acoustic microfilters, at least a portion can be positioned in parallel, in serial fashion, or in a hybrid cascading arrangement. Similarly, in arrangements in which there are two or more phononic crystal units, the units can be positioned in parallel, in serial fashion, or in a hybrid cascading arrangement.

In an interrelated aspect, a method of desalinating water comprises creating an engineered acoustic field resulting in high pressure and low pressure regions, providing at least one acoustic filter, providing a desalination membrane, and positioning a high pressure region so as to force water first through the at least one acoustic filter and subsequently through the desalination membrane thereby separating solutes from the water thereby desalinating the water.

In some implementations, an array of tubes can be provided that are each surrounded by the desalination membrane and are positioned parallel to each other. A flow chamber and one or more acoustic transducers can also be provided such that the array of tubes is positioned in the flow chamber so that the hollow portions of the tubes are in the direction of flow. The spaces between each of the tubes in the flow chamber can form an interstitial region and the acoustic transducers can be positioned so that they touch a fluid present in the flow chamber. The water to be desalinated can be present in the interstitial region and the engineered acoustic field can be oriented to force the water to be desalinated through the desalination membranes into the tubes. The water to be desalinated can be present in the tubes such that the engineered acoustic field is oriented to force the water to be desalinated through the desalination membranes into the interstitial region. The array of tubes can be packed into and/or form part of a phononic crystal or a phononic crystal system.

In a further interrelated aspect, an apparatus includes at least one acoustic microfilter and at least one phononic crystal unit. The phononic crystal unit(s) can include a guide coupled to an outlet of the at least one acoustic microfilter having a two-dimensional cubic or hexagonal configuration of circular rods (such that the phononic crystal unit is built within the guide). The phononic crystal unit(s) can also include an acoustic pressure source positioned at a first side of the guide such that the acoustic pressure source transmits acoustic energy. The acoustic pressure source can be positioned such that a box exists outside the opposite side of the guide. The acoustic microfilter(s) can filter particles from a host fluid passing there through and the at least one phononic crystal unit(s) can further filter particles from the host fluid received from the acoustic microfilter (s).

The circular rods can be between about 3.175 and about 9.525 mm in diameter. The circular rods can be embedded in urethane. The crystal system can be surrounded by urethane. The circular rods can comprise a material selected from the group consisting of alumina, stainless steel, aluminum, nylon and porous ceramic. The acoustic energy can be of a frequency between about 10 and about 200 kHz.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
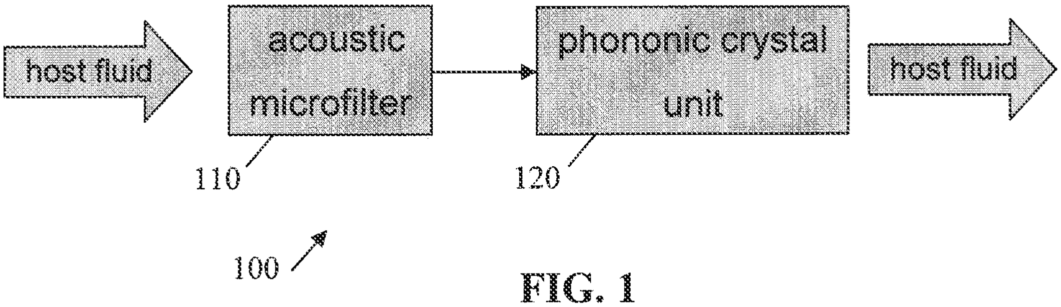
FIG. 1 is a diagram illustrating a combined acoustic microfilter and phononic crystal unit system.

The current subject matter utilizes at least one acoustic filter in combination with at least one phononic crystal unit to selectively remove/separate particles within a host fluid. Examples of acoustic filters utilizing acoustophoresis can be found in commonly owned U.S. patent application Ser. Nos. 12/947,757, 61/261,686, 13/085,299 and 61/342,307, the contents of all of these applications are hereby fully incorporated by reference. Examples of phononic crystal units can be found in commonly owned U.S. patent application Ser. Nos. 13/162,463 and 61/355,421, the contents of which are hereby fully incorporated by reference. Further details regarding both the acoustic filters and the phononic crystal units are provided below. With reference to FIG. 1, a block diagram 100 that comprise an acoustic microfilter 110 and a phononic crystal unit 120. As illustrated, a host fluid containing particulate (such as sea water), enters the acoustic microfilter 110 where a portion of the particulate is filtered or otherwise separated from the host fluid. Thereafter, the output of acoustic microfilter 110 is supplied to the phononic crystal unit 130 which further filters/separates particles from the host fluid. While diagram 100 of FIG. 1 illustrates a single acoustic microfilter 110 and a single phononic crystal unit 120, it will be appreciated there can be a number of differing arrangements including an array of one unit or both unit, cascading filters (multiple host fluid streams are combined after being filtered in parallel), and the like.

In one implementation, the combination of the acoustic microfilter 110 and the phononic crystal unit 120 can be used as part of a desalination system for a water purification process. With this arrangement, individual acoustic microfilters can be combined in series and parallel to increase capture efficiency and volume, respectively. Similarly, phononic crystal desalination units can be assembled in parallel to increase processing volume and speed.

Both of the acoustic filters and the phononic crystal units utilize acoustophoresis, a low-power, no-pressure-drop, no-clog, solid-state approach to particle removal from fluid dispersions: i.e., it is used to achieve separations that are more typically performed with porous filters, but it has none of the disadvantages of filters. As used herein, acoustophoresis can be used to sort particles of different sizes, density, or compressibility in a single pass through an acoustophoretic cavity.

An acoustophoretic separator can be created by using a piezoelectric acoustic transducer and an opposing reflection surface (or a second transducer) to set up a resonant standing wave in the fluid of interest. The ultrasonic standing waves create localized regions of high and low pressure, corresponding to high and low density of the fluid. Secondary phase contaminants are pushed to the standing wave nodes or antinodes depending on their compressibility and density relative to the surrounding fluid. Particles of higher density and compressibility (e.g., bacterial spores) move to the nodes in the standing waves; secondary phases of lower density (such as oils) move to the antinodes. The force exerted on the particles also depends on their size, with larger particles experiencing larger forces.

The current subject matter uses acoustophoresis for separations that combine (i) very small particles—micron-sized bacterial spores, or micron-sized oil droplets; (ii) high-volume flowing systems—“bench-scale” flow rates currently demonstrated are up to 250 milliliter/minute for bacterial spores; 2 liter/minute for micron-sized oil droplet collection from water; and/or (iii) low particle concentrations—$10^{10}$ spores per liter (or lower), a volume fraction of only $3\times10^{-6}$; oil droplets as a few volume percent in water. Acoustophoresis enables tailoring and control of the acoustic frequency and applied power, control of the flow velocities across a channel, geometry and positioning of the acoustic transducer and reflector in the flow channel, and the geometry of the collection region.

The separation can be achieved by capture of the small particles or droplets in a resonant acoustic cavity that is embedded in the flow system. The particles (or droplets) move only the few hundred microns to a node (or antinode) in the acoustic standing wave, and gradual agglomeration occurs as more particles are captured.

When sufficient accumulation has occurred, under some conditions buoyancy or gravity takes over, and the accumulated particles may fall or droplets will rise to the surface. In general for small particles (bacterial spores) at low particle densities, the particles will remain suspended at small amounts of particle agglomerations; the flow rate is high enough that a large accumulation will be collected from the flow. For these particle (bacterial spore) collection systems, one can use a stop/drop cycle to collect the spores.

Figure 2:
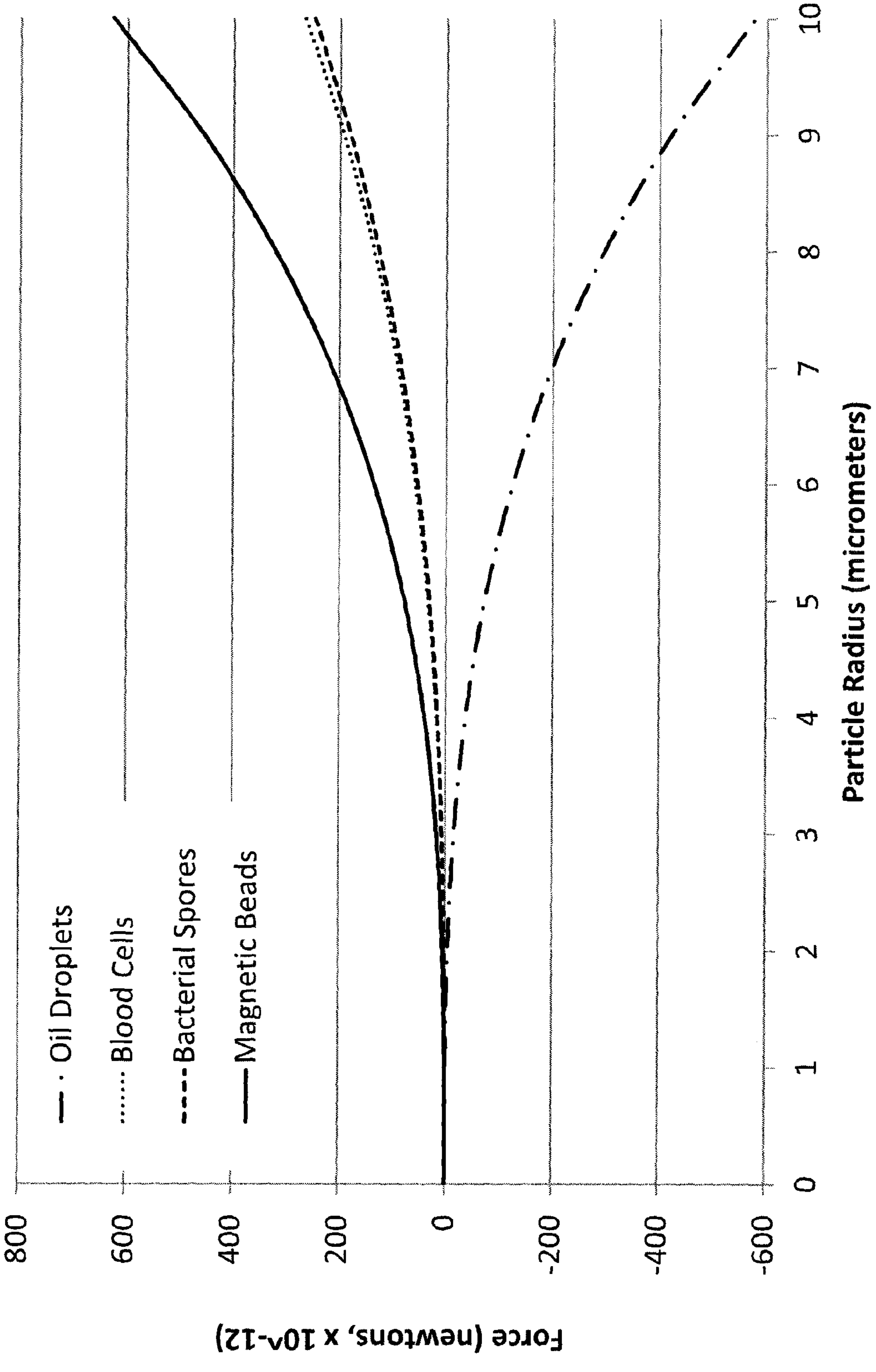
FIG. 2 is a diagram illustrating acoustic radiation force operating on micron-size particles as a function of the particle (or droplet) radius.

The acoustic radiation force ($F_{ac}$) acts on the secondary-phase particles (or fluid droplets), pushing them to the nodes (or antinodes) of the acoustic standing wave. The magnitude of the force depends on the particle density and compressibility relative to the fluid medium, and increases with the particle volume. FIG. 2 is a diagram 200 that illustrates the acoustic force that operates on four different secondary phases in water as a function of the particle (or droplet) radius. The four secondary phases are hexanes (a mixture of hydrocarbons, a model for oils), red blood cells (a model for biological cells), bacterial spores (also a model for polystyrene beads such as are used for flow cytometry), and paramagnetic polystyrene beads (used for various biological capture and separation protocols).

Acoustophoresis is the separation of a second phase (or phases) from a host fluid using sound pressure to create the driving force. An ultrasonic transducer operating at a fixed frequency $f=\omega/2\pi$ can be used to set up an acoustic standing wave in a fluid-filled cavity. For a simple standing wave, the acoustic pressure p is characterized as a function of position (x) and time (t), $$p(x,t)=P\cos(kx)\sin(\omega t), \quad (1)$$

where P is the acoustic pressure amplitude; k is the wavenumber ($2\pi/\lambda$, where $\lambda$ is the wavelength), and $\omega$ is the angular frequency. The pressure of the acoustic wave can produce an acoustic radiation force $F_{ac}$ on secondary-phase elements according to $$F_{ac} = X\pi R_p^3 k \frac{P^2}{\rho_f c_f^2}\sin(2kx). \quad (2)$$

X is the acoustic contrast factor, defined by $$X = \frac{1}{3}\left[\frac{5\Lambda - 2}{1+2\Lambda} - \frac{1}{\sigma^2\Lambda}\right], \quad (3)$$

where A is the ratio of the fluid to particle density and $\sigma$ is the ratio of the speed of sound in the fluid to the particle. $R_p$ is the particle radius, $\rho_f$ is the density of the fluid medium, $c_f$ is the speed of sound in the fluid, k is the wave vector, and P the maximum amplitude of the acoustic pressure as given in Eq (1).

TABLE 1

Properties of water and 4 selected secondary phases

| Material | ρ (density) (kg/m3) | c (speed of sound) (m/s) | Λ (dimensionless) | X (dimensionless) |
|---|---|---|---|---|
| Water | 1000 | 1509 | — | — |
| Hexanes | 720 | 1303 | 0.72 | −0.402 |
| Blood Cells | 1125 | 1900 | 1.125 | 0.185 |
| Bacterial Spores | 1100 | 1900 | 1.1 | 0.173 |
| Magnetic beads | 2000 | 1971 | 2.0 | 0.436 |

The diagram 200 of FIG. 2 shows the forces for an applied acoustic frequency of 1 MHz (half the frequency we are now using capture of micron-sized particles) and an acoustic pressure of 0.5 MPa maximum at the antinodes (readily achieved in water).

Figure 3:
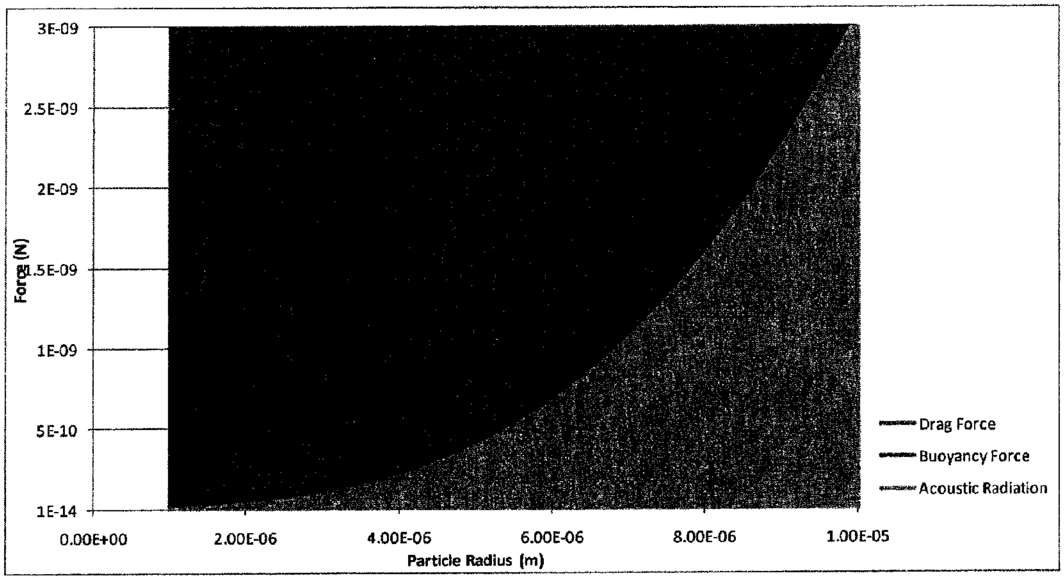
FIG. 3 is a diagram illustrating acoustic radiation force, drag force, and buoyancy force as a function of particle radius for oil droplets (baby oil) in water, in which the frequency is 2.5 MHz, the acoustic pressure amplitude is 1 MPa, and the flow velocity is 1 mm/s.

FIG. 3 is a diagram 300 that shows a similar analysis specifically for oil droplets (baby oil) of varying size. The frequency is fixed at 2.5 MHz (similar to what we have now found for most effective capture of micron-sized particles) and the acoustic pressure amplitude at 1 MPa.

For comparison to the acoustic force, in diagram 300 of FIG. 3, the fluid drag force is plotted for a flow field with a flow velocity of 1 mm/s in water. The fluid drag force $F_d$ is given by $$F_d=6\pi\mu R_p(u_f-u_p) \quad (4)$$

where $\mu$ is the dynamic viscosity of water, $u_f$ is the water flow velocity vector and $u_p$ is the particle velocity vector (and $R_p$ the particle radius, as before). The buoyancy force is also shown on the graph. The buoyancy force is given by $$F_b = \frac{4}{3}\pi R_p^3 g(\rho_f - \rho_p), \quad (5)$$

where g is the gravitational acceleration, $\rho_p$ is the particle density, and $\rho_f$ is the fluid density.

As diagram 300 indicates, the acoustic radiation forces are of the same order as the fluid drag force for particle size of the order of 2 microns. Fluid drag force scales linearly with particle radius whereas acoustic radiation force scales as the cube of particle radius—i.e., scales with linearly with volume. Higher acoustic intensities and/or frequencies can be used to offset a decrease in acoustic radiation force as a result of smaller particle sizes. Similarly, lowering the fluid velocity results in a lower fluid drag force (at the cost of smaller volumes processed).

Ultrafiltration Application Examples. The current inventors successfully trapped *Bacillus cereus* bacterial spores (a model for anthrax) at 15% efficiency in an acoustophoretic cavity embedded in a flow system that can process drinking water at rates up to 60 mL/minute (1 cm/second linear flow). The concentration ratio was as high as 1000 in their single-pass, small-scale prototype acoustocollector.

Figure 4:
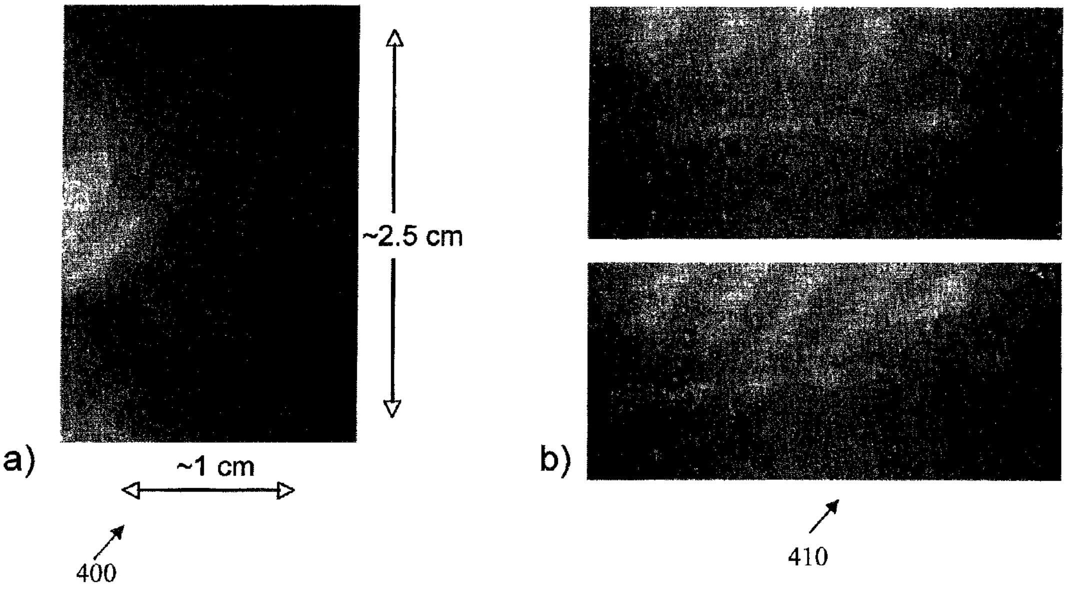
FIG. 4A is a photomicrograph of acoustophoretic trapping of dyed *B. cereus* spores in flowing water.
FIG. 4B is a photomicrograph of acoustophoretic trapping of oil droplets in the same acoustocollector used in FIG. 3A.

FIG. 4(*a*) is a photomicrograph 400 of acoustophoretic collection of dyed *B. cereus* spores in a flowing water stream. The spores are about 1.5. times.0.5 micron in size, with volume $V=3\times10^{-19}$ $m^3$; typical spore concentrations were about $10^{10}$/liter. In FIG. 4(*a*)—the transducer is at the top, just out of the image; the column of trapped spores is about 2.5 cm high.times.1 cm wide. The ultrasonic pressure nodes are seen as the horizontal planes in which the spores are captured; the water flow is from left to right.

A flat circular transducer was used in the acoustocollector that generated the photomicrograph 400 of FIG. 4(*a*). The radial component of the pressure field of this transducer is described by a Bessel function and the axial component is described by a cosine function. The radial component acts to hold the captured particles in the column against the fluid flow. In the present apparatus, spores are collected in the acoustic cavity, and thereafter collected by turning off the water flow and the acoustic power so that the agglomerated spores fall into a collection recess in the bottom of the acoustic chamber.

In FIG. 4(*b*) is a photomicrograph 410 showing the same acoustocollector configured for collection of oil droplets. In this case the flow is from top to bottom, with the transducer at the left and reflector at the right. The oil was dispersed using a surfactant, so the resulting droplets are only a few microns in size. In this case, as can be seen in the figure, the captured oil eventually reaches an agglomerated size such that buoyancy forces result in the oil rising to the top (against the water flow).

Energy requirements. The energy requirements 1.0 $E^4$ kW-hr/gal that we measure for collection from water are based on the experimentally measured electrical power delivered to the transducer. Therefore, this measured power takes into account all loss mechanisms in our system, including transducer losses, heating, and acoustic absorption. Pumping energy requirements are not included, since these depend heavily on other factors; these will be included in an overall system analysis as we learn more about the specifics of a particular application such as produced water. The energy requirements are likely comparable for any other particle separation process where a certain volume of fluid needs to be pumped, with the caveat that any flow restriction (which we do not have in the acoustocollector) or requirement for high speed flow (e.g., for hydrocyclone separations) will increase it relative to our requirements.

Experimental acoustic parameters. Even though reasonably large acoustic amplitudes were observed, on the order of 1 MPa, the current system basically operates in the linear regime. This is indicated by the acoustic Mach number $M=u_{ac}/c_f$, where $u_{ac}$ is the acoustic velocity amplitude, or $M=P_{ac}/r_f c_f^2$. So for an acoustic pressure amplitude of 1 MPa, one can find a Mach number of 0.0004, indicating that the system is far removed from any nonlinear acoustic effects.

The 1-MPa acoustic pressure amplitude can be used as a typical value of acoustic pressure amplitude in the current system but is by no means an upper limit. The current system can operate well below cavitation threshold values.

Scalability. To address scalability, it is noted that a 1 mm/s flow velocity in a 0.3 by 0.3 m flow channel results in a daily flow rate of 50 barrels. The 1 mm/s flow velocity is by no means an upper limit to the achievable flow velocities in the current system.

The current subject matter enables a low energy technique for acoustic filtration. This technique is capable of capturing various particles in the size range of 0.2 to 100 microns. Further, at the acoustic pressure nodes the pressure is high-enough (typically, ~1 MPa) to crush bacterial cells. The pressure will cause the released biopolymers from the crushed organisms to be agglomerated on to other particles found in real water sources. This arrangement enhances ultrafiltration and addresses the membrane fouling problem associated with membrane distillation.

Low Energy Pressurization. The phononic crystal units utilize phononic crystals which are the acoustic analog of photonic crystals. Sound waves propagated through air propagate in the same way that an elastic wave along a lattice of point masses connected by springs with an elastic force constant E. This force constant is identical to the modulus of the material. With phononic crystals of materials having differing modulus the calculations are more complicated.

The elastic force constant is of key importance so that one can deduce that a key factor for acoustic band-gap engineering is impedance mismatch between periodic elements comprising the crystal and the surrounding medium. When an advancing wave-front meets a material with very high impedance it will tend to increase its phase velocity through that medium. Likewise, when the advancing wave-front meets a low impedance medium it will slow down. One can exploit this concept with periodic (and handcrafted) arrangements of impedance mismatched elements to affect acoustic waves in the crystal—essentially band-gap engineering.

For inhomogeneous solids, the wave equation can be given by $$\frac{\partial^2 u_j^i}{\partial t^2} = \frac{1}{\rho_j}\left\{\frac{\partial}{\partial x_i}\left(\lambda\frac{\partial u_j^i}{\partial x_l}\right) + \frac{\partial}{\partial x_l}\left[\mu\left(\frac{\partial u_j^i}{\partial x_l} + \frac{\partial u_j^l}{\partial x_i}\right)\right]\right\}$$

where $u^i$ is the $i^{th}$ component displacement vector. The subscript j is in reference to the medium (medium 1 or medium 2); λ, μ are the Lame coefficients, ρ is the density, and the longitudinal and transverse speed of sound are given by $$c_l = \sqrt{(\lambda + 2\mu)/\rho}$$

-continued $$c_t = \sqrt{\mu/\rho}$$

The Lame coefficients can be expressed as Young's modulus E.

$$E_t = \rho c_t^2 = \mu$$

$$E_t = \rho c_t^2 = \lambda + 2\mu$$

Given the importance of Young's modulus to elastic vibrations in lattices, a numerical survey of materials, lattice spacing, packing arrangements, and crystal orientations was conducted. From compiled graphical results, it was observed that as the Young's modulus increases, the width of the first (lowest frequency) band-gap also increases. This trend is observed for both cubic (X and M direction) and hexagonal crystals (K and M directions) at several filling fractions and rod diameters. Intensely high-pressure modulations in the phononic crystal were observed. These are known as eigen modes, and are seen in diagram 500 of FIG. 5. From these results, it was concluded that one could exploit the high pressure nodes for membrane desalination.

Figure 5:
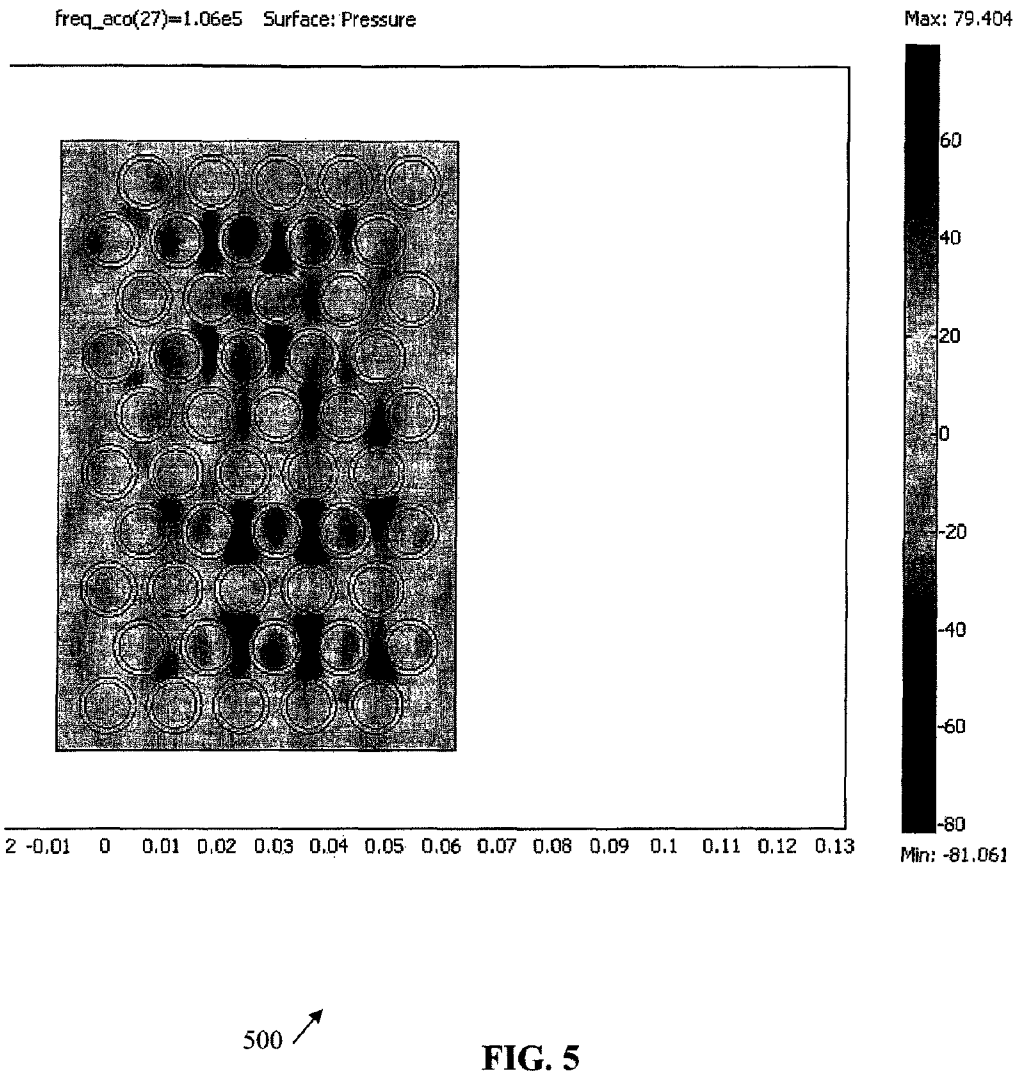
FIG. 5 is a diagram illustrating pressure modulations in a phononic crystal desalination system.

Diagram 500 of FIG. 5 shows a parallel array of 1 cm porous ceramic tubes packed in a hexagonal array and fit into a rectangular flow chamber of about 10 cm×6 cm cross-section. Saltwater flows in the interstitial region between the tubes (perpendicular to the diagram). The tubes can be coated with a thin layer (e.g., 10 microns to 500 microns, etc.) of a polymer typically used for membrane distillation, to enable water to pass into the porous tubes, so the fresh water flows through the tubes. Acoustic transducers can be placed on the sides of a rectangular container (which in turn can be made of any material that is a non-corrosive material such as titanium, stainless steel, aluminum, etc.) where they contact the saltwater. One or more sides of the rectangle contain transducers (e.g., piezoelectric transducers such as PZT-4, PZT-8, etc.). By selecting the number of transducers (e.g., 1 to 20 transducers per side, etc.), their arrangement (e.g., linear, 2-dimensional array, etc.), and selecting the acoustic frequency (e.g., 50 kHz to 20 MHz, etc.), the packing arrangement of the tubes (e.g., hexagonal to cubic packing, etc.), the reverse operation is possible. That is, the saltwater is inside the tubes and fresh water in the interstitial regions.

As described above, high-pressure regions are observed at certain regions directly next to the ceramic tubes. These high-pressure regions force the water molecules through the membrane on the surface of the porous tube. In experiments we have been able to modulate the acoustic drive frequency so as to minimize the opposite pressure when the standing wave is out of phase with the pressure requirements for the membrane, as the system operates with only a few acoustic transducers at resonance condition, one is able to affect membrane desalination through only a few tens of watts (~20 Watt-hr/L).

Figure 6:
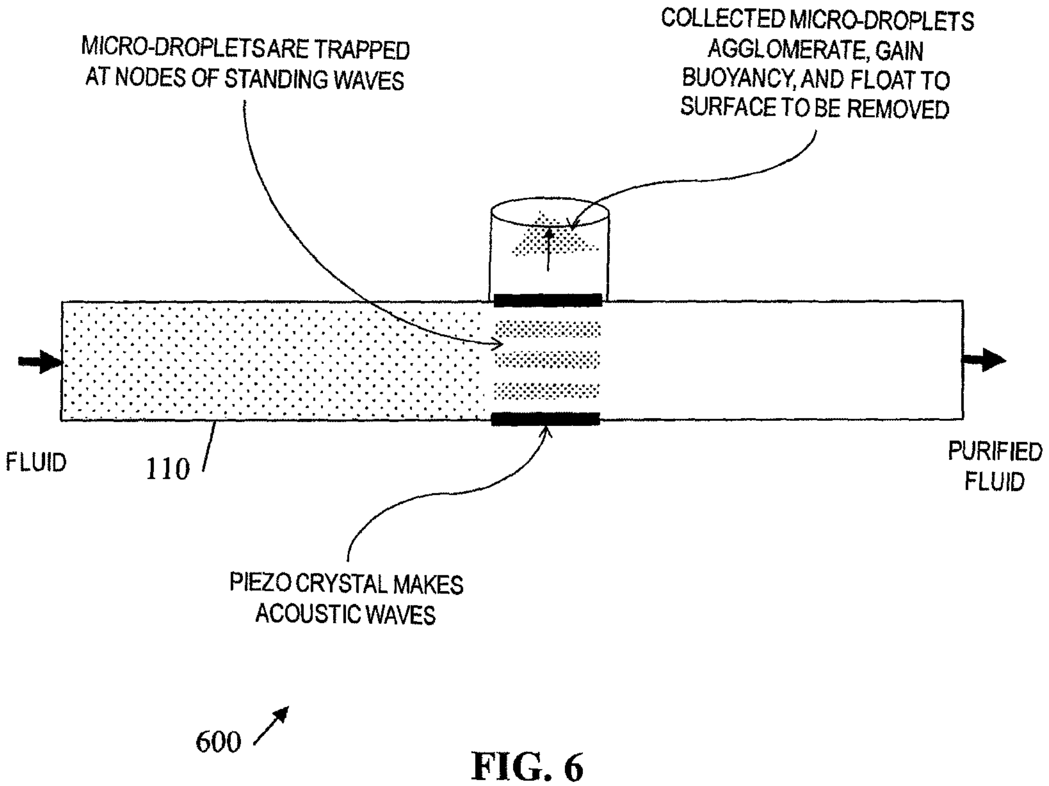
FIG. 6 is a diagram illustrating a sample acoustic microfilter.

FIG. 6 is a diagram 600 illustrating a sample acoustic microfilter 110. As shown, fluid enters the acoustic microfilter 110 whereby transducers, such as piezo crystals, make standing waves forming nodes. Particles within the fluid are trapped at the standing waves and are collected or otherwise separated (taking advantage, for example, of the buoyancy of the particles). Thereafter, filtered fluid exits the acoustic microfilter 110.

Figure 7:
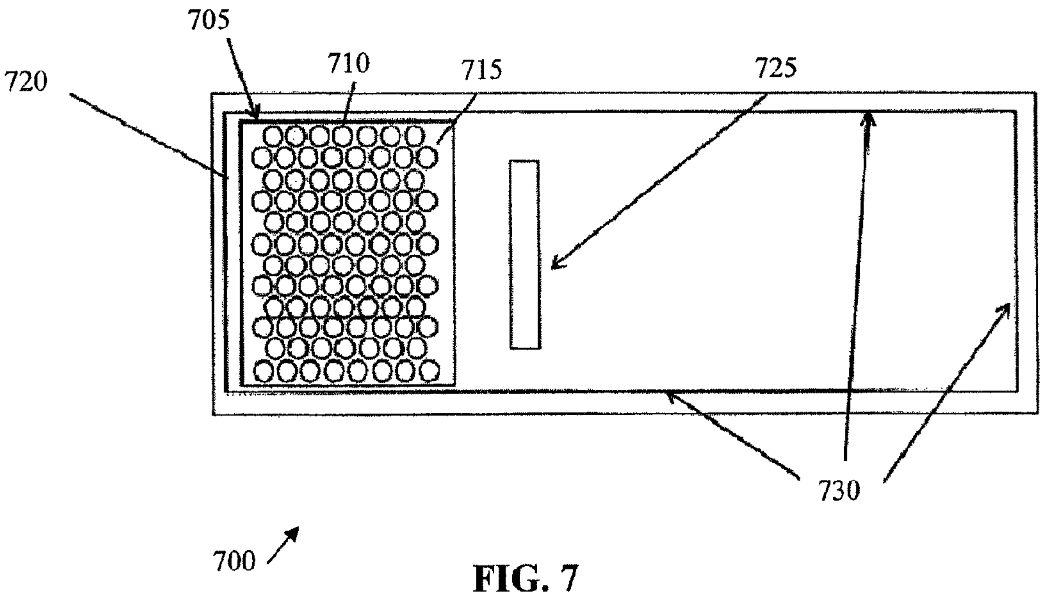
FIG. 7 is a diagram illustrating how energy gaps can be determined in phononic crystals.

The band-gaps in phononic crystals of the phononic crystal unit 120 can be a function of material composition, lattice spacing, crystal-packing arrangement, crystal orientation, and/or size of the elements in the crystal. FIG. 7 is a schematic of a configuration that can be used for computing the energy gap in various phononic crystals. As shown in FIG. 7, a guide 700 having a two-dimensional cubic or hexagonal configuration of circular rods 710 can be used to design and build the basic crystal system 705. The guide 700 can include rods 710 embedded in a urethane impedance 715 matched with water, for example, (ρ=1000 $kg/m^3$; c=1497 m/sec). To one side of the crystal system 705 can be an acoustic pressure source 720 (positioned subsequent to the acoustic microfilter 110), for example to produce plane waves. On an opposite side of the crystal system 705 can be an imaginary box 725 used for integration. In this region, the acoustic energy for preparing the transmission spectra can be integrated. The boundaries 730, except for the pressure source 720, can be water impedance. In a variation, the crystal system 705 is approximately 3.5 cm.times.5 cm surrounded by the urethane impedance 715.

The configuration, diameter, and material of the rods 710 as well as the filling fraction can all vary. The rods 710 can be in a two-dimensional cubic or hexagonal configuration. The rod diameter used can be, for example, 3.175 mm (0.125"), 6.35 mm (0.25"), and 9.525 mm (0.375"). The filling fractions used can be, for example, 0.90699, 0.403066, and 0.29613. Using all three rod diameters and all three filling fractions results in nine possible combinations. For the cubic crystals, X and M directions can be used. For the hexagonally-packed crystals, K and M directions can be used. The material of the rods 710 can vary, including alumina (ρ=3860 $kg/m^3$; c=10520 m/sec; E=$3.61\times1^{011}$ Pa), stainless steel (ρ=7850 $kg/m^3$; c=5790 m/sec; E=$1.03\times1^{011}$ Pa), aluminum (ρ=2700 $kg/m^3$; c=6420 m/sec; E=$6.9\times1^{010}$ Pa) and nylon (ρ=1130 $kg/m^3$; c=2675 m/sec; E=$2.4\times1^{99}$ Pa) or other appropriate material. In an embodiment, the material is a porous ceramic. For each rod material combination, the acoustic properties for eighteen different crystals/orientations can be analyzed. As mentioned, the frequency can vary. The frequency can be between about 10 kHz to about 20 MHz(??). In a variation, X and M directions can be used in cubic and K and M directions in hexagonal polyester (ρ=1350 $kg/m^3$; c=2100 m/sec; E=$4.41\times10^9$ Pa)) and graphite (ρ=2200 $kg/m^3$; c=3310 m/sec; E=$2.41\times10^{10}$ Pa) packed in urethane. The width and center frequency for the first band gap can be a function of the Young's modulus. The lattice spacing can be a function of the filling fraction and the rod diameter. Band gaps for materials having a modulus nearing that of the impedance will not as pronounced. For example, the band gap for nylon will not be as pronounced as alumina, steel or aluminum.

Figure 8:
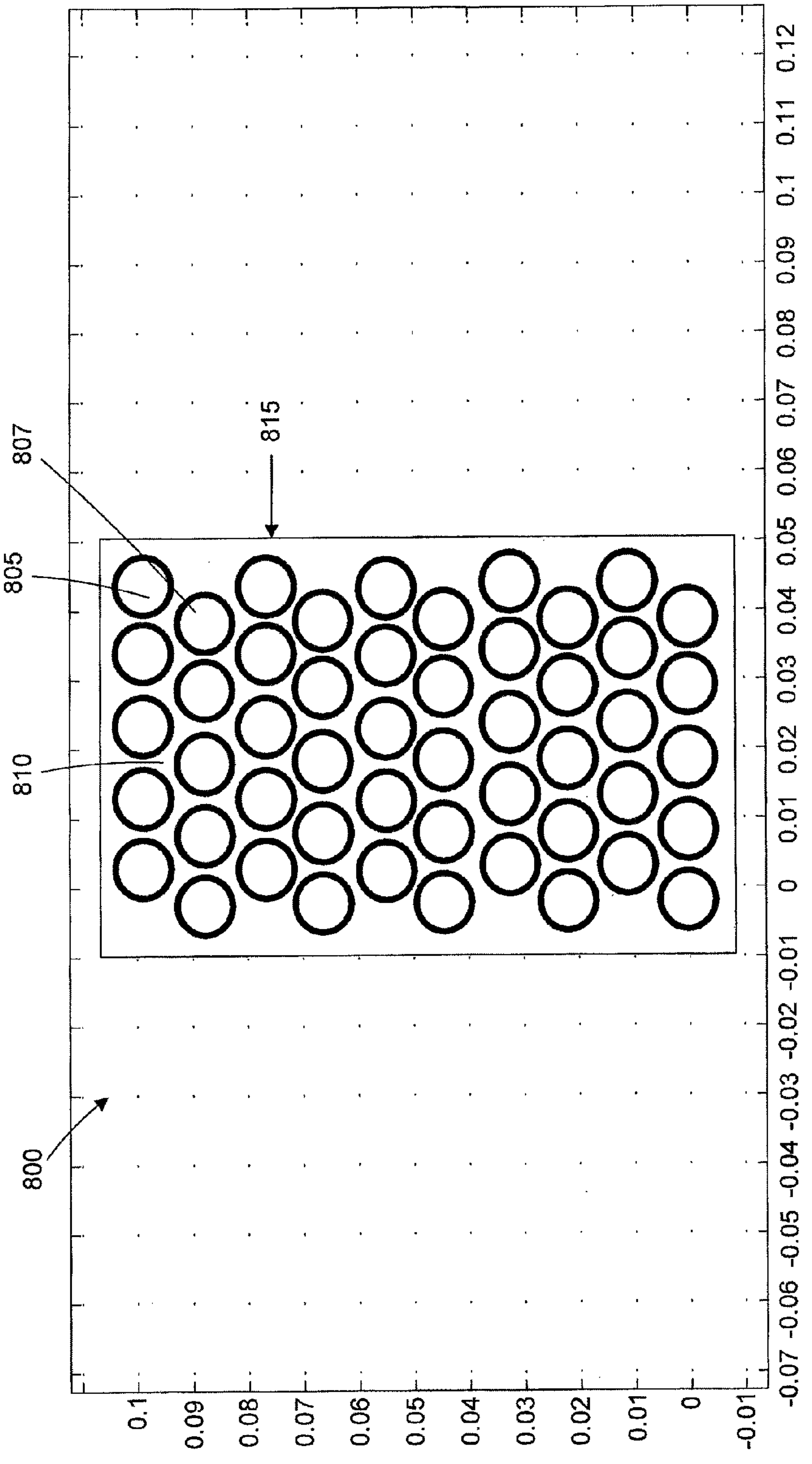
FIG. 8 is a diagram illustrating a sample phononic crystal unit.

FIG. 8 is a diagram of a phononic crystal unit 800 having a phononic crystal. The unit 800 can be a parallel array of tubes 805 coated with a membrane 807 and packed in a specific arrangement, such as a hexagonal array. The tubes 805 can be manufactured of a porous material. In one implementation, the tubes 805 are manufactured of a porous ceramic material. The membrane 807 coating the tubes 805 can be a thin layer of polymer such as a desalination polymer. The membrane 807 can allow water molecules to pass through and prevent the passage of the ionic species and dissolved organics (larger molecules) leaving them behind.

The arrangement of porous tubes 805 coated with a desalination polymeric membrane 807 can be packed into a phononic crystal. The tubes 805 can be arranged in parallel configuration or any regular polygon or circular cross-sectional shape. The arrangement of tubes 805 can be packed into a larger tube or container such as a flow chamber 815 having a generally small cross-section. The chamber 815 can be rectangular, a regular polygon, circular or other cross-sectional shape. In one variation, the cross-section of the flow chamber 215 is about 10 cm.times.6 cm. The chamber 815 can be a metal material.

Water to be desalinated can flow through the interstitial region 810 between the tubes 805 (perpendicular to the diagram) such that the inside of the tubes 805 are initially kept empty. Alternatively, water to be desalinated can flow through the inside of the tubes 805 and the interstitial regions 810 kept empty. The membrane 807 coating the tubes 805 allows fresh water to pass there through. Depending upon the configuration of the unit 800, the pure water can flow from the interstitial region 810 into and through the tubes 805. Alternatively, the pure water can flow from the tubes 805 into and through the interstitial region 810.

The arrangement of tubes 805 within the chamber 815 can be positioned adjacent to one or more acoustic transducers (not shown). The transducers can be located at one or more boundaries of the flow chamber 815 such that the transducers contact the water to be desalinated. Alternatively, the walls of the chamber 815 can act as the acoustic transducer. The packing arrangement of the tubes 805 can vary as can the number of transducers, their arrangement, and the acoustic frequency selected. In a variation, two adjacent transducers can be selected such that they cover an entire boundary or side of the flow chamber 815.

When these transducers are powered up, such as by an alternating current, they can induce a complex acoustic standing wave in the surrounding tubes 805 due to constructive and destructive interference. Stable nodes of very high-pressure differential can be produced over small spatial areas. By tuning the placement of the tubes 805 and adjusting the resonance frequency of the transducer(s), water molecules can be forced through the membrane 807 and into the empty tubes 805 (or the reverse situation, depending on tuning of the system). Each transducer can operate at a variety of resonances. The membranes 807 can be positioned at these calculated nodes of high pressure differential. Alternatively, the stable nodes of very high-pressure differential can be tuned to the location of where the membranes 807 are positioned.

While this specification contains many specifics, these should not be construed as limitations on the scope of what is claimed or of what may be claimed, but rather as descriptions of features specific to particular variations. Certain features that are described in this specification in the context of separate variations can also be implemented in combination in a single variation. Conversely, various features that are described in the context of a single variation can also be implemented in multiple variations separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

The invention claimed is:

1. A method of desalinating water, comprising:

creating an engineered acoustic field, wherein the engineered acoustic field creates high pressure regions and low pressure regions; and positioning at least one of the high pressure regions so as to force salinated water through at least one acoustic microfilter and subsequently through at least one phononic crystal unit fluidly coupled to the at least one acoustic microfilter, wherein the at least one phononic crystal unit comprises an array of parallel spaced hollow tubes, each tube being surrounded by a desalination membrane, the array of tubes being positioned in the direction of flow, the spaces between the tubes forming an interstitial region, the desalination membranes thereby separating solutes from the water to desalinate the water.

2. The method of claim 1, wherein the engineered acoustic field is oriented to force the salinated water from the interstitial region through the desalination membranes into the tubes.

3. The method of claim 1, wherein the engineered acoustic field is oriented to force the salinated water from the tubes through the desalination membranes into the interstitial region.

4. The method of claim 1, wherein the at least one acoustic microfilter comprises:

a first flow chamber with an inlet and an outlet through which is flowed the salinated water;

two or more ultrasonic transducers embedded in a wall of the first flow chamber or located outside the flow chamber wall; and two or more reflectors corresponding to each transducer located on the opposite wall of the first flow chamber from each corresponding transducer, the combination of each ultrasonic transducer and corresponding reflector forming a standing acoustic wave at a different ultrasonic frequency optimized for a specific range of particle sizes to selectively filter particles in the fluid.

5. The method of claim 4, wherein the at least one acoustic microfilter comprises a two dimensional array of transducers.

6. The method of claim 4, wherein the at least one acoustic microfilter comprises a linear array of transducers.

7. The method of claim 1, wherein the at least one phononic crystal unit further comprises:

a second flow chamber with an inlet and an outlet through which is flowed the salinated water after being filtered by the at least one acoustic microfilter;

one or more ultrasonic transducers embedded in a wall of the second flow chamber or located outside a second flow chamber wall; and one or more reflectors corresponding to each transducer located on the opposite wall of the second flow chamber from each corresponding transducer, wherein the ultrasonic transducer/reflector pairs in combination with the array of tubes further selectively filter particles from the fluid;

wherein the array of parallel spaced hollow tubes is located within the second flow chamber.

8. The method of claim 7, wherein there are at least two transducers in each phononic crystal unit that cover an entire boundary or side of the second flow chamber.

9. The method of claim 1, wherein the tubes are made up of a porous material.

10. The method of claim 1, wherein the array of parallel spaced tubes is positioned in a hexagonal array.

11. The method of claim 1, wherein the array of parallel spaced tubes in positioned in a linear array.

12. The method of claim 1, wherein there are two or more phononic crystal units positioned in parallel.

13. The method of claim 1, wherein there are two or more phononic crystal unit serially positioned.

14. The method of claim 1, wherein there are two or more acoustic microfilters positioned in parallel.

15. The method of claim 1, wherein there are two or more acoustic microfilters serially positioned.

* * * * *